United States Patent [19]

Heiss

[11] 4,082,852

[45] Apr. 4, 1978

[54] COMPOSITION FOR SANITIZING OF SURFACES

[76] Inventor: Florian Heiss, Heidstucken 27, 2000 Hamburg 71, Germany

[21] Appl. No.: 390,377

[22] Filed: Aug. 24, 1973

[30] Foreign Application Priority Data

Aug. 22, 1972 Switzerland ............... 12441/72
May 16, 1973 Germany ............... 2324587

[51] Int. Cl.² ............... A01N 9/24; A61L 9/04
[52] U.S. Cl. ............... 424/317; 424/45; 424/235; 424/333; 424/334; 424/341
[58] Field of Search ............... 424/230, 235, 45, 334, 424/341, 317

[56] References Cited

U.S. PATENT DOCUMENTS 3,629,464  12/1971  Nosler et al. ............... 424/334

FOREIGN PATENT DOCUMENTS 1,067,539  5/1967  United Kingdom.

OTHER PUBLICATIONS

Chemical Abstracts, vol. 63 (1965), p. 11,431c.
Heiss, Swiss App. #12441/72, filed 8-22-72 (patent # not available).

Primary Examiner—V. D. Turner
Attorney, Agent, or Firm—Cushman, Darby & Cushman

[57] ABSTRACT

A sanitizing composition comprising a water insoluble bacteriostatic compound, a bactericidal compound, an aliphatic alcohol and water is disclosed.

21 Claims, No Drawings

COMPOSITION FOR SANITIZING OF SURFACES

This invention relates not only to the sanitizing of utensils made of plastics, but also of other materials, such as, for example, metal, wood, ceramics and the like, which come into contact with the human body.

It is known that such articles carry a large number of germs and pathogens, especially bacteria, on their surface. This phenomenon is of particular importance in the case of articles which are constantly touched by different persons without the germs being killed immediately, such as the case, for example, for door handles, lavatory seats and telephones. While lavatories, at least, are cleaned frequently, the same is not true of telephones, though, for example, coin-operated telephones or telephones in offices are constantly used by many different persons and in the course thereof are contaminated with germs of all kinds both by manual contact and by spray caused by speaking.

In all of these cases, it is possible to destroy the germs almost entirely by disinfection with a customary disinfectant. Numerous disinfectants included in the list of recommendations of the West German Ministry of Health are suitable for this purpose, for example, certain phenolic derivatives as well as agents containing aldehydes, especially agents based on formaldehyde. For sterilization or disinfection, these agents are most effective when they have a bactericidal, fungicidal and in part also a virucidal effect. However, the anti-bacterial action lasts for a very brief period so that practically immediately after disinfection the treated article can again become cotaminated.

Attempts have been made to achieve a longer-lasting antiseptic action by, for example, emulsifying the active compounds in fats. However, for the end uses of interest in the present case, such preparations are not suitable since, on contact of the articles with hands or other parts of the body, the preparations are transferred to the human skin, so that the action is of extremely limited duration. In addition, it is, as a rule, not possible to treat utensils with agents containing fats, since this produces unacceptable soiling caused by adhesion of dust.

Experiments with surface-active substances, especially quaternary ammonium compounds, which have an anti-bacterial action for a longer period, have also not proved successful. A longer-lasting action is not achieved because the active substances, on contact with perspiring skin, are removed from the surface of the treated articles.

Attempts have been made to achieve a permanent bactericidal action by applying to the surfaces a mixture which consists of a plastics material and bactericidally active organic or inorganic compounds. A durable coating is supposed to be achieved by subsequent polymerization of polycondensation of the plastics material. Such agents have not found practical acceptance because suitable systems of mutually compatible polymerizable plastics materials and bactericidal active substances are not available and because such agents lead, in addition, to a modification of the treated surfaces.

Finally, anti-microbial compositions which are supposed to exert both a bactericidal and a bacteriostatic action are known, especially for staphylococci, in spaces which are considered hazardous (hospitals, children's playschools, public lavortories and the like). These compositions contain 3 to 10 percent of phenolic compounds, 1 to 5 percent of polybromosalicylanilide, 4 to 20 percent of a cleaning agent, a complex forming agent such as ethylenediaminetetraacetic acid, 4 to 88 percent of a lower aliphatic alcohol and 3 to 75 percent of water. Also, it has already been proposed to employ for the same purpose solutions of polychlorinated phenolic compounds, for example, 2,4,4'-trichloro-2'-hydroxydiphenyl ether, in a lower aliphatic alcohol.

The activity of these last-mentioned compositions again has not proved entirely satisfactory, especially because the disinfectant action is not sufficiently broad and, hence, initially by no means all germs are completely destroyed during the treatment with compositions.

The present invention provides compositions by which utensils which frequently come into contact with the human skin can simultaneously be both completely disinfected and in addition provided with an effective anti-bacterial finish for the period between two treatments. In this way, transfer of pathogens is largely prevented. In other words, conditions necessary to destroy all the germs present are maintained for a prolonged period, and in this way the transfer of infectious diseases is prevented.

The present invention provides a composition for sanitizing surfaces of plastics or other materials which come into contact with the human body, which comprises:

a. a substantially water-insoluble bacteriostatic compound, or mixture of compounds,
b. a bactericidal compound or mixture of compounds,
c. an aliphatic alcohol with 1 to 5 carbon atoms in the molecule, and
d. water.

Preferably, the compositions also contain a non-ionic emulsifier. As the bacteriostatic compound or compounds (a), polychlorinated phenolic compounds especially 2,4,4'-trichloro-2'-hydroxydiphenyl ether, are preferred. In addition, combinations of such compounds with di-, tri- and tetra-halogenosalicylanilides, for example 3', 3', 4,5'-tetrachlorosalicylanilide, 3', 4',5-trichloro- and 3,4'-5-tribromosalicylanilide and their mixtures, or with essential oils, are particularly suitable, since theses combinations display a synergistically increased bacteriostatic action.

The bacteriocidal compound or compounds (b) preferably contain aldehyde groups, since such compounds display an outstanding anti-microbial activity coupled with a broad spectrum of action. Compounds which can be used include especially formaldehyde and formaldehyde donors, glyoxal, glyoxylic acid and mixtures of such compounds. It is surprising that these aldehyde compounds are compatible with the bacteriostatic compounds based on phenols, as it would have been expected that a considerable decrease in action would result from a condensation reaction between the two.

Bacteriostatic agents have hitherto found application predominantly in medicine and in cosmetics. In the cosmetics industry, such compounds are incorporated into appropriate formulations which are marketed as deodorant soaps, aerosol sprays or similar products. An essential factor in the longer-lasting deodorant action of these preparations is the fact that the compounds are absorbed on the human skin and stored there. A similar storage action is observed with other materials of natural origin, for example, rayon, cotton or animal wool. Investigations on the impregnation of fabrics of these materials by washing with washing powders containing bacteriostatic substances have been carried out. In the course of these, it has been found that it is possible to achieve an anti-bacterial finish by adding 1 to 3 percent by weight of bacteriostatic agents to the detergent substances in the course of a washing process. On the other hand, an analogous finishing of synthetic fiber fabrics has proved impossible because the agents are not absorbed.

Surprisingly, therefore, it has been found that the bacteriostatically active compounds employed in the present invention are absorbed on plastics and develop thereon a long-lasting bacteriostatic activity. The compositions produce an anti-bacterial impregnation which is storage stable and the impregnation remains effective even on repeated contact with human skin. Both immediately after the treatment and after repeated washing with water or after frequent touching, the contact growth index (CGI) has a value between zero and 1 according to the method of determination described in detail below.

Isopropyl myristate has proved particularly suitable as a non-ionic emulsifier. The emulsifier improves the adhesion of the bacteriostatic compound or compounds to the treated surfaces and, hence, increases the long-term action. At the same time, the emulsifier has the desired side-effect of improving the gloss of the plastics surfaces treated therewith. Other suitable non-ionic emulsifiers are polyoxyethylenesorbitan esters and fatty acid alkyl esters.

The compositions of the invention contain about 0.001 to 0.5, preferably 0.01 to 0.2, and especially about 0.1 percent by weight of bacteriostatic compound or compounds. The content of bactericidal compound or compounds is about 0.01 to 1.5, especially 0.1 to 0.5, and preferably about 0.3 percent by weight. The amount of aliphatic alcohol, preferably 1 to 3 carbon atoms, for example, ethanol, is about 60 to 90 percent by weight. The remainder of the composition consists of water, that is to say it contains about 10 to 40 percent by weight of water. The ratio of alcohol to water is preferably about 2:1 to 5:1. If an emulsifier is used, its concentration in the agent is about 0.1 to 3.0 percent by weight.

If desired, the composition can be made up as an aerosol. The customary propellant gases are directly compatible with the compositions.

Using the new compositions, effective sanitization can be achieved for a prolonged period, and because of the presence of the bactericidal compound or compounds, prior disinfection is superfluous. It was unexpected that the new compositions would be absorbed on, for example, plastics surfaces such as the material of which telephones are made (acrylonitrile/butadiene/styrene polymers) and would display a long-lasting action. For this reason only disinfection, but not effective sanitization, of utensils has hitherto been disclosed at all.

The activity of the compositions of the invention can be proved by determining the contact growth index (CGI). The bacteriological methods of investigation hitherto customary, for example the diffusion test, are unsuitable for this purpose, since the bacteriostatic substances applied are not soluble in water and hence do not diffuse into the nutrient medium and thus also do not lead to an inhibition zone. Instead, a new method of investigation had to be developed, which in principle is based on applying the substances to be investigated to a carrier, after which the latter is incorporated into a solid nutrient medium in such a way that the surface of the carrier is just covered with nutrient agar so that on the one hand an inoculation and hence bacterial growth is possible, while on the other hand the coating thickness is only a fraction of a millimeter. In this way, virtually direct contact between the substance to be tested and the types of bacteria applied results during incubation of the inoculated carrier plate. In this method, a check of the bacterial growth is provided by the fact that optimum bacterial growth must take place on the nutrient agar which is not in contact with the carrier. The process at the same time permits conclusions regarding the solubility in water of the substance investigated because bacterial inhibitions beyond the zone of the carrier, that is to say in the control zone, indicate that, because of its solubility in water, the substance to be investigated has diffused into the surrounding nutrient medium during the incubation. The CGI determined after incubation is rated in accordance with the following scale:

0 = Total inhibition over the entire contact surface
1 = Minimum growth at the edge of the contact surface
2 = Isolated micro-colonies on the contact surface
3 = A small number of micro-colonies on the contact surface
4 = Optimum growth on the contact surface, corresponding to that in the control zone The examples which follow illustrate the invention.

EXAMPLE 1

A sanitizing composition according to the invention was manufactured as follows: 2.5 ml. of 36 percent aqueous formaldehyde solution, 0.45 g. of glyoxylic acid and 0.2 g. of glyoxal were dissolved in distilled water, after which sufficient water was added to make up the total volume of the solution to 270 ml.

1.0 g. of 2,4,4'-trichloro-2'-hydroxydiphenyl ether, 10.0 ml. of isopropyl myristate and 0.5 ml. of a scent concentrate were separately dissolved in 96 percent ethyl alcohol and the solution was made up to a volume of 730 ml. by adding further alcohol.

The aqueous solution was poured into the alcoholic solution with vigorous stirring, giving a clear ready-to-use sanitizing solution.

EXAMPLE 2

A solution suitable for packing in aerosol cans was manufactured as follows:
1.091 liters of 36 percent aqueous formaldehyde solution, 0.3928 kg. of glyoxylic acid and 0.1746 kg. of glyoxal were dissolved in distilled water with warming to 60° – 80° C., and the volume of the solution was then made up to 72.44 liters.

0.4364 kg. of 2,4,4'-trichloro-2'-hydroxydiphenyl ether, 4.364 liters of isopropyl myristate and 0.2182 liter of a scent concentrate were dissolved in 96 percent ethyl alcohol, and the volume was made up to 364.16 liters.

After mixing the aqueous solution with the alcoholic solution a clear sanitizing composition was obtained, which was filled into aerosol cans. 81 g. of propellant gas (Frigen 12 and Frigen 114 in the ratio of 40:60) were used per 369 g. of the composition.

COMPARISON EXPERIMENTS

The anti-bacterial storage action of the abovementioned compositions on the surface of telephone apparatuses made of acrylonitile/butadiene/styrene polymers (Novodur) was examined by determining the CGI. for this purpose, square sheets of 2 × 2 cm edge length were sawn from the telephone apparatuses and then treated with the compositions by rubbing the surface vigorously with a cotton wool pad which was impregnated with the solution to be investigated. The CGI. was determined as described above, testing 10 strains of staphylococcus aureus, 10 strains of staphylococcus epidermis, 10 strains of escherichia coli, 10 strains of proteus spec., 10 strains of pseudomonas aeruginosa and 10 strains of aerobacter klebsiella. A solution of 0.1 percent by weight of 2,4,4'-trichloro-2'-hydroxydiphenyl ether in 70 percent by volume aqueous ethyl alcohol was used for comparison.

Test 1

First, the CGI was determined on plastic plaques treated with composition A (Example 1), composition B (Example 2) and composition C (Comparison), after drying the plaques in air. A CGI of zero was found for all the agents tested.

Test 2

After Test 1 had shown that the treatment produces an excellent effect, an investigation of the storage stability of the impregnation was carried out by treating the surface of the plastic plaques with the cotton wool pad impregnated with the composition to be tested and then incorporating the plaques into nutrient agar, and taking them out again, six times in succession. The inoculation with the various bacterial strains was carried out after the last incorporation. Because of the removal of the agar layer covering the plaque, which was necessary after each incorporation, the plaque treated with composition C now only showed a CGI of 1, whilst a CGI of zero was found for composition A and B.

Test 3

A further series of tests was carried out with the objective of simulating the conditions in practical use as naturally as possible. For this purpose, the surface of plaques were rubbed down, as previously described, with cotton wool pads which were impregnated with the solutions to be investigated. Thereafter, a total of 100 fingers were pressed against the treated surface before the plaques were incorporated into the nutrient agar. However, only one of the nutrient medium plates treated in this way was in each case inoculated with bacteria whilst a further plate served for comparison. The pairs of plates were in each case incubated for 20 hours at 37° C., after which the CGI was determined for the inoculated plate whilst in the case of the plate which had not been incubated it was possible to observe the development of the contamination germs which had been applied to the plates through contact with the fingers. The compositions of the invention proved to be fully effective because the contamination germs applied by touching were incapable of multiplying on the plaques. A CGI of 1 to 2 was found for composition C, but a CGI of zero for A and B. Hence the compositions of the invention proved to be clearly superior.

What we claim is:

1. A composition suitable for sanitizing the surface of a material which comes into contact with the human body comprising (A) a substantially water insoluble bacteriostatic halogen substituted phenol,
    (B) a bactericide which comprises a water soluble aldehyde,
    (C) an unsubstituted aliphatic alcohol with 1 to 5 carbon atoms in the molecule and
    (D) water.

2. A composition according to claim 1 consisting essentially of (A), (B), (C) and (D).

3. A composition according to claim 1 consisting essentially of (A), (B), (C), (D) and an emulsifier.

4. A composition according to claim 1 in which B comprises formaldehyde, a formaldehyde donor, glyoxal or glyoxylic acid.

5. A composition according to claim 4 wherein B is a mixture of formaldehyde, glyoxal and glyoxylic acid.

6. A composition according to claim 5 wherein the bacteriostatic comprises 2,4,4'-trichloro-2'-hydroxydiphenyl ether.

7. A composition according to claim 4 wherein the bacteriostatic comprises 2,4,4'-trichloro-2'hydroxydiphenyl ether.

8. A composition according to claim 1 wherein the bacteriostatic (A) comprises said halogen substituted phenol and a di, tri or tetra-halogenosalicylanilide.

9. A composition according to claim 1 including an essential oil.

10. A composition according to claim 1 wherein the alcohol is ethyl alcohol.

11. A composition according to claim 4 comprising 0.001 to 0.5% by weight of (A), 0.01 to 1.5% by weight of (B), 60 to 90% by weight of (C) and 10 to 40% by weight of (D).

12. A composition according to claim 11 comprising 0.01 to 0.2% by weight of (A) and 0.1 to 0.5% by weight of (B).

13. A composition according to claim 12 wherein the ratio of (C) to (D) is 2:1 to 5:1.

14. A composition according to claim 7 comprising 0.001 to 0.5% by weight of (A) and 0.01 to 1.5% by weight of (B).

15. A composition according to claim 1 comprising 0.001 to 0.5% by weight of (A) and 0.01 to 1.5% by weight of (B).

16. A composition according to claim 1 which additionally contains a non-ionic emulsifier.

17. A composition according to claim 1 in which the bacteriostatic (A) comprises 2,4,4'-trichloro-2'-hydroxydiphenyl ether.

18. A composition according to claim 1 comprising 0.001 to 0.5 percent by weight of bacteriostatic compound or compounds (A) 0.01 to 1.5 percent by weight of bactericidal compound or compounds (B) 60 to 90 percent by weight of aliphatic alcohol (C) and 10 to 40 percent by weight of water.

19. A composition according to claim 18 which also comprises 0.1 to 3.0 percent by weight of emulsifier.

20. A composition according to claim 19, in which the emulsifier is isopropyl myristate.

21. A composition according to 1 in the form of an aerosol.

* * * * *